United States Patent [19]

Hsiao

[11] Patent Number: 4,555,399
[45] Date of Patent: Nov. 26, 1985

[54] ASPIRIN TABLET

[75] Inventor: Charles H. Hsiao, Cooper City, Fla.

[73] Assignee: Key Pharmaceuticals, Inc., Miami, Fla.

[21] Appl. No.: 587,533

[22] Filed: Mar. 8, 1984

Related U.S. Application Data

[63] Continuation-in-part of Ser. No. 553,256, Nov. 18, 1983, abandoned.

[51] Int. Cl.$^4$ .................. A61K 9/28; A61K 9/36; A61K 31/60
[52] U.S. Cl. ........................................ 424/35; 424/16; 424/80; 514/165
[58] Field of Search ................ 424/16, 19-22, 424/35, 80, 230

[56] References Cited

U.S. PATENT DOCUMENTS

| | | | |
|---|---|---|---|
| 2,811,483 | 10/1957 | Aterno et al. | 424/21 |
| 2,853,420 | 9/1958 | Lowey | 167/82 |
| 2,887,440 | 5/1959 | Greminger et al. | 424/35 |
| 2,928,770 | 3/1960 | Bardani | 167/82 |
| 3,081,233 | 3/1963 | Enz et al. | 167/82 |
| 3,109,775 | 11/1963 | Shepard et al. | 167/82 |
| 3,133,863 | 5/1964 | Tansby | 424/35 |
| 3,247,066 | 4/1966 | Milosovich | 167/82 |
| 3,256,111 | 6/1966 | Singiser | 424/35 |
| 3,341,416 | 9/1967 | Anderson et al. | 424/35 |
| 3,344,029 | 9/1967 | Berger | 167/82 |
| 3,383,236 | 5/1968 | Brindamour | 424/35 |
| 3,388,041 | 6/1968 | Gans et al. | 424/35 |
| 3,400,185 | 9/1968 | Kohnle et al. | 264/117 |
| 3,488,418 | 1/1970 | Holliday et al. | 424/35 |
| 3,524,910 | 8/1970 | Holliday et al. | 424/35 |
| 3,632,739 | 1/1972 | Kornblum | 424/20 |
| 3,773,920 | 11/1973 | Nakamoto et al. | 424/19 |
| 3,835,221 | 9/1974 | Fulberth et al. | 424/20 |
| 3,907,983 | 9/1975 | Seth | 424/35 |
| 3,917,813 | 11/1975 | Pedersen | 424/35 |
| 3,922,339 | 11/1975 | Shear | 424/19 |
| 3,951,851 | 4/1976 | Kitajima | 421/35 |
| 4,016,254 | 4/1977 | Seager | 424/271 |
| 4,083,949 | 4/1978 | Benedickt | 424/19 |
| 4,138,475 | 2/1979 | Mc Ainsh et al. | 424/20 |
| 4,167,558 | 9/1979 | Shoth et al. | 424/35 |
| 4,173,626 | 11/1979 | Dempski et al. | 424/19 |
| 4,248,858 | 2/1981 | Guley et al. | 424/21 |
| 4,259,314 | 3/1981 | Lowey | 424/19 |
| 4,321,253 | 3/1982 | Beatty | 424/35 |
| 4,341,759 | 7/1982 | Bogentoft et al. | 424/21 |

FOREIGN PATENT DOCUMENTS 109438  1/1940  Australia ................ 424/20

OTHER PUBLICATIONS

Green et al., J. Pediatrics 98(5): 832–834, May 1981, "Absorption Characteristics of Sustained Release Theophylline Capsules Administered in Applesauce".
Weinberger, J. Pediatrics 92(1): 1–7, Jan. 1978, Theophylline for Treatment of Asthma.

*Primary Examiner*—Shep K. Rose
*Attorney, Agent, or Firm*—Wegner & Bretschneider

[57] ABSTRACT

A tablet, which readily disintegrates in gastric fluid to give aspirin crystals coated with a polymeric film preventing the aspirin crystals from contacting the stomach wall but not preventing access of gastric fluid to the aspirin contained within the polymer film, which consists of a plurality of aspirin crystals 20–60 mesh in size coated with about 3–10% by weight of a polymeric mixture comprising from about 1.5 to about 15 parts by weight ethylcellulose and about one part by weight hydroxypropylcellulose; a compression aid; a disintegrant; and a tableting aid.

7 Claims, No Drawings

ASPIRIN TABLET

This application is a continuation-in-part of my application Ser. No. 553,256, filed Nov. 18, 1983, now abandoned.

The present invention relates to an improved aspirin tablet. More particularly, it relates to an aspirin tablet having a substantially lessened irritant effect on the gastric mucosa.

It is well known that aspirin and other salicylates can cause gastric ulceration and even hemorrhage in animals and in humans. One approach to minimizing the local irritant effect of aspirin on the gastric mucosa is to use enteric-coated aspirin formulations. However, the enteric coating is dissolved/digested in the small intestine, and the aspirin particles exposed can cause irritation to the mucosa of the small intestine. Enteric-coated formulations are not suitable for persons requiring the fast onset of aspirin's analgesic and/or antipyretic activity, e.g., rapid relief from headache, pain and/or fever.

Green, The Journal of New Drugs, pages 294–304, September–October 1966, teaches microspherules of enteric-coated aspirin compressed into a readily disintegratable tablet. Although the tablet disintegrates in the stomach, the aspirin does not become available for absorption until the enteric coating is dissolved in the small intestine. Dissolution of the coating and absorption of the aspirin is described as slow and the microspherules are said to behave like a sustained-dosage form. Green's tablets are particularly suited for patients where large doses of aspirin must be provided over long periods of time.

U.S. Pat. No. 3,954,959 teaches mixing small particles of a medicament with a buffer and other adjuvants, and then coating the mixture with a non-digestible, film-forming, acrylic polymer. Stomach juice and then intestinal juice slowly leach out the medicament at a relatively constant rate independent of body fluid pH.

U.S. Pat. No. 4,193,985 teaches coating subunits of a medicament, such as aspirin, with a non-digestible polymer membrane wherein the medicament is leached out as the polymer subunit passes through the intestinal tract. The patentees indicate that a tablet containing such subunits can be prepared but no description of tablet preparation is given.

The present invention provides an aspirin tablet which, when ingested, rapidly disintegrates in the stomach into numerous polymer-coated aspirin crystals whereby the aspirin is absorbed in the stomach with minimal contact with the gastric mucosa. The crystals of aspirin are coated with a polymeric film which permits entrance of gastric fluid to dissolve the aspirin contained inside of the film but which prevents the aspirin crystals from coming into contact with the lining of the stomach.

In its broadest aspect, the present invention is a tablet consisting of a plurality of aspirin crystals 20-60 mesh in size coated with about 3-10% by weight of a polymeric mixture comprising from about 2.5 to about 15 parts by weight ethylcellulose and about one part by weight hydroxypropylcellulose; a compression aid; a disintegrant; and a tableting aid.

In another aspect, the present invention is a tablet which readily disintegrates in gastric fluid to give aspirin cyrstals coated with a polymeric film preventing the aspirin crystals from contacting the stomach wall but not preventing access of gastric fluid to the aspirin contained within the polymer film, which consists of a plurality of aspirin crystals 20-60 mesh in size coated with about 3-10% by weight of a polymeric mixture comprising from about 2.5 to about 15 parts by weight ethylcellulose and about one part by weight hydroxypropylcellulose; a compression aid; a disintegrant; and a tableting aid.

Although the aspirin used as the "seed" for the tablet of the present invention may be compounded with minor amounts of other ingredients, in accordance with a preferred aspect of the present invention, it is contemplated that pure aspirin crystals will be used. The crystals should have a relatively uniform particle size distribution ranging from about 20 to about 60 mesh with 40 mesh preferred. It is contemplated that only minor amounts of the crystals will fall outside this range.

The polymeric coating requires a major component of ethylcellulose and a minor component of hydroxypropylcellulose, with the weight ratio of ethylcellulose to hydroxypropylcellulose be at least about 2.5. It is contemplated that the weight ratio being from about 2.5:1 to about 15:1, with a preferred range being from about 3.5:1 to about 12:1, and still more preferably about 4:1. By providing a proper balance of ethylcellulose to hydroxypropylcellulose, the polymer film of the present invention remains intact in the stomach (and afterwards) but is permeable to gastric fluid which dissolves and leaches out the aspirin contained therein. The weight of the polymeric coating is from about 3 to about 10% of the total weight of the polymerically coated aspirin crystal with 5% being preferred. Lesser amounts, particularly below 3%, give rise to bare spots by disruption of the coating during the compression step, and increases the likelihood of solid aspirin coming into contact with the lining of the stomach. The rate of absorption of the aspirin decreases as the weight of the polymer coating increases and becomes unsatisfactory above about 10%.

The thus coated aspirin crystals are mixed with a compression aid, such as microcrystalline cellulose; a disintegrant, such as cross-linked sodium carboxymethylcellulose, cross-linked polyvinylpyrrolidone or sodium starch glycolate; and a tableting aid, such as hydrogenated vegetable oil, mineral oil, or the like. By incorporation of a compression aid, less force is required to compress the mixture into tablets thereby minimizing disruption of the polymer film coating the aspirin crystals. Incorporation of a disintegrant ensures fast disintegration of the tablet in the stomach. The tableting aid serves its usual purpose of "lubricating" the resultant tablet for easy release when the mixture described above is tableted in conventional, commercially available, tableting equipment.

It should be emphasized that the tablet of the present invention is not a conventional sustained release tablet. However, some delay in dissolution and subsequent absorption of the aspirin is "built in" to minimize the likelihood of solid or "concentrated" aspirin from coming into contact with the wall of the stomach. Essentially only "liquid" or "dilute" aspirin reaches the gastric mucosa.

The tablet of the present invention intended for a single dosage unit for adult use contains about 1000 mg of acetylsalicylic acid (the usual adult aspirin tablet contains 5 grains or 325 mg of acetylsalicylic acid) and can be scored for a smaller dose.

The following examples serve to illustrate the invention:

EXAMPLE I (a) 10,000 gm aspirin crystals, having a size of between 30 and 60 mesh, were placed in a twelve inch air suspension coating column (Wurster column manufactured by Glatt, West German) preheated to 40° C. with a polymer solution which contained 420.8 gm ethylcellulose ["Ethocel N-10" (Dow)] and 105.2 gm hydroxypropylcellulose ["Klucel LF" (Hercules)], 1503 ml methanol and 6012 ml chloroform. The coating solution was sprayed at a liquid feed rate of 150 ml/minute under a pressure of 4 bars and inlet air temperature of about 60° C. After all of the polymer solutions had been applied, the coated aspirin crystals were dried for 10 minutes and screened to about 40 mesh.

(b) 2106 gm of the coated aspirin crystals, 118 gm of micro crystalline cellulose [Avicel pH 101 (FMC)], 94 gm of cross-linked polyvinylpyrrolidone [Crospovidone NF] and 22 gm hydrogenated vegetable oil U.S.P. were thoroughly mixed. The mixture was compressed into tablets using a Stokes tablet machine equipped with plain capsule-shaped scored punches, 0.310×0.744×0.061 inches at 1500 psi. Tablet weight was 1170 mg.

(c) The polymer-coated aspirin crystals so prepared were tested according to the standard dissolution procedure in simulated gastric fluid for 1 hour and then in simulated intestinal fluid for the remaining testing period as described in U.S.P. XX. The results observed are tabulated below:

| Time (hours) | % Aspirin Released |
| --- | --- |
| 1 hour | 27.8 |
| 2 | 65.4 |
| 4 | 99.2 |

EXAMPLE II (a) using the general procedure of Example I, 10,000 gm of 20–40 mesh aspirin crystals were coated with 602.4 gm of ethylcellulose and 150.6 gm of hydroxypropylcellulose in 2152 ml of methanol and 8608 ml of chloroform. Coating conditions were similar but the liquid feed rate was 200 ml/min and the pressure 2.5 bars.

(b) About 2150 gm of the coated aspirin crystals, 120 gm of micro crystalline cellulose, 96 gm of cross-linked polyvinylpyrrolidone and 24 gm of hydrogenated vegetable oil were thoroughly mixed and the mixture tableted.

(c) The dissolution rate of the tablets in simulated gastric fluid for 1 hour and then in simulated intestinal fluid is tabulated below:

| Time (hours) | % Aspirin Released |
| --- | --- |
| 1 | 17.3 |
| 2 | 50.6 |
| 4 | 82.6 |
| 6 | 92.8 |
| 8 | 97.6 |
| 10 | 98.5 |

I claim:

1. A tablet that readily disintegrates in gastric fluid to give aspirin crystals coated with a polymeric film preventing the aspirin crystals from contacting the stomach wall but not preventing access of gastric fluid to the aspirin contained within the polymer film, which consists of a plurality of aspirin crystals 20–60 mesh in size coated with about 3–10% by weight of a polymeric mixture of about 1.5 to about 15 parts by weight ethylcellulose and about one part by weight hydroxypropylcellulose; a compression aid; a disintegrant; and a tableting aid.

2. A tablet according to claim 1 wherein the crystals are about 40 mesh in size.

3. A tablet according to claim 1 wherein the ratio of ethylcellulose to hydroxypropylcellulose is 4:1.

4. A tablet according to claim 1 containing about 1000 mg of aspirin.

5. A tablet according to claim 1 wherein said compression aid is microcrystalline cellulose.

6. A tablet according to claim 1 wherein said disintegrant is cross-linked polyvinylpyrrolidone.

7. A tablet according to claim 1 wherein said tableting aid is hydrogenated vegetable oil.

* * * * *